United States Patent [19]

Tsai

[11] Patent Number: 4,935,256

[45] Date of Patent: Jun. 19, 1990

[54] PROCESS FOR MAKING GREEN TEA SOLIDS

[75] Inventor: Chee-Hway Tsai, West Chester, Ohio

[73] Assignee: Procter & Gamble Company, Cincinnati, Ohio

[21] Appl. No.: 429,666

[22] Filed: Oct. 31, 1989

[51] Int. Cl.$^5$ .............................................. A23F 3/14
[52] U.S. Cl. .................................. 426/330.3; 426/435; 426/597
[58] Field of Search ............... 426/597, 655, 435, 425, 426/429, 495, 330.3, 455, 330.5, 453, 454

[56] References Cited

U.S. PATENT DOCUMENTS

| | | | |
|---|---|---|---|
| 3,392,028 | 7/1968 | Vuataz | 426/597 |
| 4,051,267 | 9/1977 | Jongeling | 426/597 |
| 4,410,556 | 10/1983 | Lunder | 426/435 |
| 4,472,441 | 9/1984 | Clark | 426/435 |
| 4,490,402 | 12/1984 | Lunder | 425/435 |

FOREIGN PATENT DOCUMENTS

| | | | |
|---|---|---|---|
| 0201000 | 11/1986 | European Pat. Off. | |
| 60-13780 | 1/1985 | Japan | 426/597 |
| 1184512 | 10/1985 | U.S.S.R. | 426/597 |

*Primary Examiner*—Carolyn Paden
*Attorney, Agent, or Firm*—Rose Ann Dabek; Jerry J. Yetter; Richard C. Witte

[57] ABSTRACT

A process for isolating and purifying green tea solids in good yield is described. The process uses food approved solvents and provides flavanols with less green/grassy flavor. A less bitter and less astringent flavanol pectin complex is also prepared using pectins, cellulose, gums or sugars.

17 Claims, No Drawings

PROCESS FOR MAKING GREEN TEA SOLIDS

TECHNICAL FIELD

This invention relates to a process for isolating green tea solids, in particular catechins, epicatechins and other flavanols in a good yield. Also disclosed is a process for co-drying these flavanols with cellulose, pectins, or gums or sugars, to mask their bitter flavor.

BACKGROUND OF THE INVENTION

Teas, both green and black teas, contain caffeine, but the caffeine in these drinks does not appear to be as physiologically available as in coffee. In fact, green tea is believed to have a relaxing benefit owing to the flavanols (i.e., the catechins and epicatechins) present in green tea. Green tea has had several other physiological benefits attributed to it. It is believed to lower blood pressure and to have other soothing and healing benefits. It is believed that the flavanols are responsible for these benefits.

The catechins and epicatechins, also known as flavanols, are obtained by the extraction of plants, e.g. green tea and related plants. Plants containing catechins are known to those skilled in the art. These flavanols are natural substances present in a variety of plants including green teas and herb teas.

Green tea includes materials obtained from the tea plant *Camellia sinensis*, for instance, freshly gathered tea leaves, fresh green tea leaves that are dried immediately after gathering, fresh green tea leaves that have been heat treated before drying to inactivate any enzymes present, and aqueous extracts of these leaves. Green tea materials are tea leaves and their extracts which have not undergone substantial fermentation to create black tea.

The flavanols can be extracted from either a single plant or mixtures of plants. Examples of the most common flavanols which are obtained from extraction from the tea plants and other members of the *Catechu gambir* or (Uncaria family) are catechin, epicatechin, gallocatechin, epigallocatechin, epicatechin gallate, epigallocatechin gallate.

The flavanols can be extracted from green tea or other natural source by hot water, but then have to be isolated from the water mixture. Up to the present, this isolation has been done in low yield, less than 30%, and through the use of chlorinated solvents, e.g chloroform and methylene chloride. In addition, these solids often have a grassy or green flavor associated with them. The chlorinated solvents remove grassy flavors, but the use of these solvents for materials to be used for human consumption is being questioned.

It has now been found that use of a mixture of solvents which are food approved can satisfy both the deflavoring of the green tea and also isolate the catechins from the water extract. Yields as high as 70% to 80% recovery are achieved.

It has also been found that co-drying these deflavored flavanols with cellulose, pectins, sugars and gums produces a flavanol with a less bitter taste.

Therefore, it is an object of this invention to provide a process for isolating and deflavoring flavanols from green teas and other natural sources.

It is also an object of this invention to provide dried flavanols with a less bitter taste.

These and other objects will become apparent from the description herein.

All percentages are by weight unless otherwise indicated.

SUMMARY OF THE INVENTION

A process for isolating flavanols from natural sources is disclosed. The process comprises:
(1) extracting a flavanol source with hot water to remove the flavanols;
(2) deflavoring the flavanols by extracting the aqueous solution with a mixture of hexane and a low molecular weight alcohol;
(3) extracting the flavanols from the remaining aqueous phase with ethyl acetate; and
(4) recovering the flavanols from the ethyl acetate.

The flavanols have a bitter and astringent taste. One way to mask this taste is to complex the flavanols with a pectin or gums or other cellulosic material. The deflavored flavanol can be co-dried with a pectin, hydrolyzed pectin, sugar or cellulosic material.

DETAILED DESCRIPTION OF THE INVENTION

Definitions

As used herein, the term "comprising" means various components can be conjointly employed in the processes of the present invention. Accordingly, the term "comprising" encompasses the more restrictive terms "consisting essentially of" and "consisting of".

As used herein "flavanols" or "catechins" means primarily catechin, epicatechin, and their derivatives. These derivatives include the sugar salts, sugar esters, gallate esters, and other edible physiologically available derivatives. Green tea solids contain these catechins.

As used herein, the term "aqueous phase" refers to the water phase in an extraction process. It includes water solutions of tea extracts, flavanols, and other water mixtures.

As used herein, the term "low molecular weight alcohol" means an organic alcohol having from 1 to about 4 carbon atoms. Preferred alcohols include ethanol, propanol, isopropyl alcohol and n-butanol.

As used herein, the term "masking agents" includes PVP (polyvinylpyrrolidone), pectins, cellulosic materials, gums, and sugars, cellulose, cellulose derivatives, e.g. carboxymethyl cellulose (CMC), hydrolyzed pectins and high methoxypectins, hydroxypropyl methylcellulose, gums, and nucleic acids.

Processing

A. Extraction of Flavanols

Green tea leaves or other botanical sources of flavanols are extracted with hot water. Preferably, the flavanol source is counter-currently extracted in a batch or continuous process. The extraction yield of the flavanols is from about 10% to about 35%. In addition to the botanical sources, any tea solid can be used. However, as noted above, the process for making black teas and other processed teas, e.g. instant teas, polymerizes the catechins and therefore decreases the yield of the flavanols. The flavanol solution can be concentrated or dried to a powder for storage.

B. Deflavoring

The flavanol or green tea solids are dissolved in water (if a powder). Preferably the aqueous solution contains from about 15% to about 35% green tea solids. The aqueous solution is extracted with a mixture of food grade hexane and one or more low molecular weight alcohols. A ratio of from about 1.5:1 to about 10:1 hexane to low molecular weight alcohol is used. The ratio is on a volume to volume basis. Preferably a ratio of hexane to alcohol of about 5:1 to about 3:1 is used.

Any low molecular weight alcohol can be used. However, since these materials are being consumed, ethanol, n-butanol and isopropyl alcohol are preferred. The subsequent processing removes all traces of these materials, but food grade alcohols and hexane should be used.

The extraction is carried out at room temperature (65° F. (18° C.) to 95° F. (35° C.). For maximum deflavoring, the extraction should be repeated two to three times. The preferred ratio of organic solvent to aqueous phase should be about 1:1. A ratio of 0.5:1 to about 2:1 organic phase to water phase can be used.

The organic phase is discarded. For economic reasons, the hexane and the alcohol can be recovered by distillation or evaporation. The green and grassy notes should be removed before the solvent is reused in the extraction process. The green and grassy flavors are due to the presence of chlorophylls, other sterols and plant materials.

C. Isolation of Flavanols

The aqueous phase is separated and then extracted with ethyl acetate. Again food grade ethyl acetate should be used. A volume of 0.5:1 to abut 2:1 ethyl acetate to water is used. The aqueous layer is preferably extracted twice. The organic layers (ethyl acetate) are combined. The flavanols are present in the ethyl acetate layer.

The solvent is removed by evaporation or distillation. Preferably this will be done at reduced pressure to avoid over heating the flavanols which have been isolated by this process. The dried green tea solids or flavanols can then be added to beverages or other food materials.

D. Complexation with masking agents

The flavanols can add a bitter taste to foods and beverages. This is particularly notable in beverages which are not ordinarily astringent or bitter. This bitter taste can be modified by adding polysaccharides including cellulose, pectin, and various gums to the beverage. PVP or polyvinylpyrrolidine can also be used as a masking agent. These materials form a reversible complex with the flavanols and mask the bitterness, but release the flavanols in the stomach or intestines for absorption.

Nucleotides and nucleic acids, as well as other alkaloids can also be used to control the bitterness. Other materials such as sugar can also be used to mask the bitter flavor of the flavanols.

The solid flavanols are redissolved in 0.1 volumes to 1 volume of water. This solution can be stripped to half volume to form a concentrate which is then mixed with masking agents, e.g. pectins, cellulose, nucleic acids, nucleotides and gums.

The cellulosic derivations that can be used include carboxymethyl cellulose, hydroxypropyl methyl cellulose and natural food approved celluloses. Gums include gum arabic, guar gum, gum acacia, locust bean gum and carragennan can be used.

The preferred masking agent is a partially hydrolyzed pectin. Pectinase treatment lowers the viscosity of the beverage to which the final pectin/flavanol complex is added. Partially hydrolyzed pectin also complexes with flavanols better than the un-treated pectin. The hyrolysis of the pectin is accomplished by treating pectin with a pectinase for a time sufficient to lower the viscosity of the solution. Treatment with a 0.05% (V/V) solution of pectinase for about 30–45 minutes has been found to be sufficient.

Sugars can also be co-dried with flavanols from a water solution. The preferred sugar is sucrose which can cocrystallize with the flavanols. Other sugars which form glasses or can form syrups with flavanols include fructose, dextrose, maltose and lactose.

The concentrate and the masking agent are mixed in a ratio of 1:2 to 2:1 (weight to weight basis). The material is then dried by freeze drying or spray drying. A powder is obtained. This powder is then mixed with the beverage or food.

Any conventional spray drying or freeze drying equipment can be used. The temperature should be controlled to keep the flavanols from polymerizing and oxidizing.

The masking agents and flavanols can also be used as a syrup. A concentration of from about 10% to about 40% flavanols, 10% to about 40% masking agent and from about 20% to about 80% water is used.

The following examples are illustrative and are not meant to be limiting to this invention.

EXAMPLE 1

Commercial green tea leaves are extracted with water counter-currently using a series of five Mr. Coffee ® automatic brewers. From 900 g of dry leaves and 13.5 liters of water, 2000 ml of tea concentrate containing 10% solids is obtained. The concentrate is evaporated to about half of its volume in a vacuum rotary evaporator at 60° C. and under 30 mm Hg pressure, and spray-dried subsequently to tea powder. About 200 g of dry green tea solids are obtained.

Green tea solids (200 g) are dissolved in 2000 ml of warm water and are mixed thoroughly with 3000 ml of hexane/butanol mixture (4/1, v/v) in a 6 liter separatory funnel. The mixture is allowed to separate into two layers. The organic layer (top) is separated; it is a dark green color. The aqueous phase is extracted a second time with the same volume of hexane/butanol. Again the organic layer is discarded.

To the aqueous layer 3000 ml of ethyl acetate is added and mixed thoroughly. After separation into two layers, the organic layer (top) is collected. It is a dark brown. The ethyl acetate extraction is repeated and both fractions of ethyl acetate are combined. The solvent is removed in a vacuum rotary evaporator at 40° C. under 50 mm Hg pressure. The dry residues are dissolved in 400 ml distilled water, evaporated to 200 ml at 60° C. under 50 mm Hg pressure, and freeze-dried. After 47 g of dry green tea solids is obtained and it contains nearly 95% catechins based vanillin analysis (described below).

Vanillin Analysis

The vanillin method is specific for catechins because the vanillin reagent reacts only with the hydroxyl groups on the phloroglucinol unit (A ring) of catechin. It can be used to measure the content of catechins and the degree of polymerization.

Material and Method

Reagents

Vanillin reagent: 1.0 g vanillin is dissolved in 100 ml of 70% sulfuric acid (v/v). Prepare fresh every three days.

Standard epicatechin solution: Prepare fresh epicatechin stock solution at 1.0 mg/ml in 50% ethanol.

Procedure:

Dilute epicatechin standard to 0.05, 0.10, 0.20, 0.30 mg/ml from the stock solution with distilled water. Dissolve samples in 50% ethanol at the following concentrations: Green tea solids—0.4–0.6 mg/ml; green tea catechins 0.1–0.2 mg/ml. The sample or standard solution (0.25 ml) is mixed with 0.75 ml of distilled water in a test tube. Add 4.0 ml of vanillin reagent to the test tube which has been placed in iced water to keep the temperature below 35° C. The sample and reagent are mixed well and cooled. This mixture is incubated at room temperature for 15 minutes. Read absorbance at 500 nm using (1.0 ml distilled water+4.0 ml vanillin reagent) as a blank in an absorption spectrophotometer.

Do not allow more than 0.1 ml of alcohol in the reaction because alcohol appears to change the intensity of the red color complex.

Epigallocatechin and epicatechin gallate appear to have the same molar absorptivity as epicatechin when complexed with vanillin under acidic conditions. Therefore, a molecular weight ratio of 1.5 is used to convert the molar absorption into the weight of flavanol solids in an epicatechin standard.

The precision of vanillin assay is determined to be 1.3% cv based on three separate runs of standard epicatechin.

EXAMPLE 2

As described in Example 1, 2000 ml of 10% tea concentrate is obtained from the counter-current extraction. It is mixed with 3000 ml of methylene chloride/ethanol mixture (4/1, v/v), and extracted three times with 3000 ml of ethyl acetate. The process produces 37 g of dry catechins.

The process of this invention therefore produces an additional 10 gm of dried catechins. This one-third higher yield.

EXAMPLE 3

Commercial high methoxypectin, 25 g, is suspended in 400 ml of warm water (104° F., 40° C.). To this suspension, 0.2 ml of pectinase (Rohapect TF, Rohm Tech, Inc. Malden, MA) is added. The mixture is incubated at ambient temperature with continuous stirring for about 30 minutes. At the end of the incubation, the enzyme is inactivated by heating the mixture to boiling. The flavanols, 39 g, from Example 1 are mixed into the cooled pectin slurry. This mixture is mixed for about 10 minutes and then freeze dried to a powder. From this process, 63.5 g of dry catechin-pectin complex is prepared. When this complex is dissolved in distilled water, it is less astringent and less bitter than an equivalent concentration of catechin alone.

EXAMPLE 4

Spray dried green tea solids, 200 g, was dissolved in 2 liters of warm water and extracted the same way as in Example 1. An aqueous flavanol solution weighing 254 g was produced (200 ml in volume.) This concentrate contains 49.8 g of catechins as determined using a refractometer and dry catechins as a standard. The liquid catechin solution is mixed with a high methoxy pectin slurry (500 ml containing 36 g of dry pectin). This slurry is then treated with pectinase as in Example 3. The final freeze dried mixture is ground to a powder. The process generated 78 g of dry pectin-catechin complex.

EXAMPLE 5

A beverage syrup is made by mixing the following ingredients:

| Ingredient | Weight |
| --- | --- |
| Distilled Water | 9,444 grams |
| Phosphoric Acid (75%) | 50 grams |
| Citric Acid | 8 grams |
| Cola Flavor | 186 grams |
| Liquid Fructose (77% by weight solids) | 8,483 grams |
| Sucrose | 726 grams |
| Caffeine | 9 grams |
| *Green tea solids | 153 grams |

*The purified green tea solids contain 4.3% caffeine and 95.7% catechins.

This syrup is mixed with carbonated water to prepare a carbonated cola beverage (117.3 grams of syrup is diluted with 353.5 grams of carbonated water at a level of 3.2 to 3.4 volumes of carbon dioxide). The level of caffeine is about 0.02%.

EXAMPLE 6

A beverage syrup is made by mixing the following ingredients:

| Ingredient | Weight |
| --- | --- |
| Distilled Water | 9,444 grams |
| Phosphoric Acid (75%) | 50 grams |
| Citric Acid | 8 grams |
| Cola Flavor | 186 grams |
| Liquid Fructose (77% by weight solids) | 8,483 grams |
| Sucrose | 726 grams |
| Caffeine | 9 grams |
| Flavanol/pectin complex | 250 grams |

This syrup is mixed with carbonated water to prepare a carbonated cola beverage (117.3 grams of syrup is diluted with 353.5 grams of carbonated water at a level of 3.2 to 3.4 volumes of carbon dioxide).

The beverage is less astringent tasting than the beverage of Example 5.

What is claimed is:

1. A process for isolating flavanols from natural sources comprising:
   (1) extracting a flavanol source with hot water to remove the flavanols;
   (2) deflavoring the flavanols by extracting the aqueous solution with a mixture of hexane and a low molecular weight alcohol wherein the ratio of hexane to alcohol is from about 10:1 to about 1.5:1;
   (3) extracting the deflavored aqueous phase with ethyl acetate; and
   (4) recovering the flavanols from the ethyl acetate.

2. A process according to claim 1 wherein said flavanol source is green tea.

3. A process according to claim 2 wherein said low molecular weight alcohol is selected from the group consisting of ethanol, n-propyl alcohol, isopropyl alcohol, n-butanol and mixtures thereof.

4. A process according to claim 3 wherein said alcohol is n-butanol.

5. A process according to claim 4 wherein the ratio of hexane to alcohol is from about 5:1 to about 3:1.

6. A process according to claim 5 wherein the ratio of hexane/alcohol mixture to aqueous phase in step (2) is from about 0.5:1 to about 2:1.

7. A process for masking the bitter flavors of flavanols by co-drying a mixture comprising flavanols and a masking agent.

8. A process according to claim 7 wherein said masking agent is selected from the group consisting of pectins, cellulose, cellulose derivatives, hydrolyzed pectin and methoxylated pectin and mixtures thereof.

9. A process according to claim 8 wherein said pectin is a pectin hydrolyzed with pectinase.

10. A process according to claim 7 wherein said masking agent is polyvinylpyrrolidone.

11. A process according to claim 10 wherein said pectin and said flavanol are mixed in a ratio of 1:2 to 2:1 (weight to weight basis).

12. A process according to claim 7 wherein co-drying is freeze-drying.

13. A process according to claim 7 wherein co-drying is spray-drying.

14. A process according to claim 7 wherein said masking agent is selected from the group consisting of gum arabic, gum acacia, carrageenan, locust gum and mixtures thereof.

15. A process according to claim 14 wherein the co-drying is freeze drying.

16. A process according to claim 7 wherein said masking agent is sucrose.

17. A process according to claim 16 wherein said sucrose and flavanols are spray-dried from a solution comprising;
 (a) about 10% to about 40% sucrose;
 (b) about 10% to about 40% green tea solids; and
 (c) about 20% to about 80% water.

* * * * *